US00PP36204P2

(12) United States Plant Patent
MacKenzie

(10) Patent No.: US PP36,204 P2
(45) Date of Patent: Oct. 15, 2024

(54) ***PANICUM* PLANT NAMED 'Noneulby'**

(50) Latin Name: *Panicum virgatum*
Varietal Denomination: Noneulby

(71) Applicant: Hortech, Inc., Nunica, MI (US)

(72) Inventor: David MacKenzie, Nunica, MI (US)

(73) Assignee: HORTECH, INC., Nunica, MI (US)

( * ) Notice: Subject to any disclaimer, the term of this patent is extended or adjusted under 35 U.S.C. 154(b) by 0 days.

(21) Appl. No.: 18/421,015

(22) Filed: Jan. 24, 2024

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
CPC ... A01H 5/12; A01H 5/02; A01H 5/00; A01H 6/46
See application file for complete search history.

*Primary Examiner* — June Hwu
(74) *Attorney, Agent, or Firm* — Penny J. Aguirre

(57) ABSTRACT

A new cultivar of *Panicum* plant named 'Noneulby' that is characterized by its compact, slightly broad and upright plant habit, its average of 76 cm in height and 61 cm in width in the landscape, its foliage that is blue in color, its flowers that are silver in color and changing to purple in color, and its flowers that are held partially above the foliage (about 1/3).

1 Drawing Sheet

Botanical classification: *Panicum virgatum.*
Varietal denomination: 'Noneulby'.

BACKGROUND OF THE INVENTION

The present invention relates to a new and distinct cultivar of *Panicum virgatum* and will be referred to hereafter by its cultivar name, 'Noneulby'. 'Noneulby' represents a new cultivar of switchgrass, an ornamental grass grown for landscape use.

The new cultivar of *Panicum* was derived from an ongoing controlled breeding program conducted by the Inventor in Nunica, Michigan. The goals of the breeding program include developing new cultivars of *Panicum* with novel ornamental traits that include strong stature, compact habits, and unique foliage or flower colors.

'Noneulby' originated as a seedling that arose from open pollination in a production field containing numerous cultivars and proprietary seedlings of *Panicum virgatum* varieties at the Inventors' nursery in September of 2019. The collected seeds were pooled prior to planting in an evaluation field plot and therefore the parentage is unknown. 'Noneulby' was selected as a single unique plant in September of 2021 from amongst the resulting seedlings.

Asexual propagation of the new cultivar was first accomplished by the Inventor by rhizome division in Nunica, Michigan in September of 2021. Asexual propagation by division and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Noneulby' as a unique cultivar of *Panicum.*

1. 'Noneulby' exhibits a compact, slightly broad and upright plant habit.
2. 'Noneulby' exhibits an average of 76 cm in height and 61 cm in width in the landscape.
3. 'Noneulby' exhibits foliage that is blue in color.
4. 'Noneulby' exhibits flowers that are silver in color and changing to purple in color.
5. 'Noneulby' exhibits flowers that are held partially above the foliage (about 1/3).

'Noneulby' can be most closely compared to *Panicum cultivars*, 'Dewey Blue' (not patented), and 'Heavy Metal' (not patented). 'Dewey Blue' and 'Heavy Metal' are both similar to 'Noneulby' in having blue foliage and an upright plant habit. 'Dewey Blue' differs from 'Noneulby' in having silver flowers that stay silver in color, a taller plant height, and a tighter plant habit. 'Heavy Metal' differs from 'Noneulby' in having silver flowers that stay silver in color, a tighter plant habit, and a slightly taller plant height.

BRIEF DESCRIPTION OF THE DRAWING

The accompanying color photograph illustrates the overall appearance and distinct characteristics of the new *Panicum*. The photograph was taken of a 5-year-old plant of 'Noneulby' as grown outdoors in a trial garden in Nunica, Michigan. The photograph provides a side view of a plant of 'Noneulby' in bloom. The colors in the photograph are as close as possible with the photographic and printing technology utilized and the color values cited in the Detailed Botanical Description accurately describe the colors of the new *Panicum.*

DETAILED BOTANICAL DESCRIPTION OF THE PLANT

The following is a detailed description of five-year-old plants of the new cultivar as grown outdoors in a trial garden in Nunica, Michigan. The phenotype of the new cultivar may vary with variations in environmental, climatic, and cultural conditions, as it has not been tested under all possible environmental conditions. The color determination is in accordance with The 1986 and 2007 Royal Horticultural Society Colour Chart, London, England, except where general color terms of ordinary dictionary significance are used.

General description:

*Blooming period*.—From August until October in Michigan.

*Plant type*.—Herbaceous perennial grass.

*Plant habit*.—Compact, slightly broad and upright, nonlodging clump of foliage with upright flowering spikes held partially above the foliage (about 1/3).

*Height and width or spread*.—An average of 76 cm in height (including inflorescences) and 61 cm in spread as grown in the landscape for 5 years.

*Hardiness zone*.—At least in U.S.D.A. zones 4 to 9.

*Diseases*.—Good resistance to rust (caused by *Puccinia emaculata*) has been observed.

*Root description*.—Fibrous and fine, deeply rooted, a blend between 161A and 164C in color.

*Propagation*.—Rhizome division and tissue culture.

*Rhizomes*.—An average of 3 cm in length and 0.5 cm width and 155A in color.

*Growth rate*.—Moderate for a *Panicum*.

*Time required for root development*.—From 2-inch wide divisions; up to 4 weeks for root initiation with a fully rooted plant in a 3.5-inch container produced in an average of 6 weeks.

Culm (stem) description:

*General*.—Cylindrical, hollow pith, thin but strong, held erect.

*Culm number*.—An average of 8 in an 8-cm container, forming a tight clump.

*Culm color*.—A blend between 136C and 137B in summer, 162A with base 161B to 161C in winter, ranges from 6.4 cm to 10.2 cm of exposed area between leaf nodes.

*Culm size*.—An average of 6.4 mm in diameter and 61 cm in height from the base to the base of the peduncle.

*Culm surface*.—Glabrous, smooth, and slightly striate.

*Internode length*.—An average of 7.6 cm.

Foliage description:

*Leaf shape*.—Narrowly lanceolate.

*Leaf division*.—Simple.

*Leaf margin*.—Entire, scaberulous.

*Leaf base*.—Sheathed to base of the node.

*Leaf venation*.—Parallel, not distinguishable in color from leaf coloration.

*Leaf width*.—An average of 9.5 mm at widest section.

*Leaf length*.—Blade; an average of 36.8 cm, sheathed portion; an average of 10.6 cm.

*Leaves per culm*.—An average of 5 on flowering culms.

*Leaf color*.—Upper and lower surfaces 189A.

*Leaf surface*.—Glabrous, dull, and slightly striate on both surfaces.

*Ligule*.—An average of 1.6 mm in height and 3.2 mm in width, color on both surfaces; 186A at the top, covered in fine hairs on the on inner surface that protrude from the top, NN155C in color.

Flower description:

*Inflorescence type*.—Dense, spreading panicle at terminus of stem, symmetrical, typically 8-flowered spikelet with lower spikelet male and upper spikelet hermaphroditic.

*Inflorescence color*.—Overall color of the raceme is 138B in early summer, maturing to 63C, turns to 165C in the late fall.

*Inflorescence size*.—An average of 21 cm in length and 1.3 cm in width.

*Inflorescence arrangement*.—Upright.

*Spikelet description*.—An average of 320 per panicle, oval to elliptic in shape, an average of 9.5 mm in length and 6.4 mm in width, awn present; an average of 0.5 mm in length and 61A in color, lower glume; an average of 4 mm in length and 1 mm in width, upper glume and lower lemma; an average of 4.5 cm in length and 1 mm width, color; glumes and lemma upper and lower surface; a blend between 144D and 157B suffused with 165B near the base, palea; an average of 1.5 mm in length and 0.5 mm in width, translucent and glossy, color upper and lower surface a blend between 155C and 157D, glumes, lemma, and palea are oval to elliptic in shape and convex with all surfaces glabrous and smooth.

*Rachis*.—An average of 5.1 cm in length from last leaf, raceme portion; an average of 27 cm in length and 1 mm in width, glabrous and smooth surface, 189B in color, lateral branches (peduncle-like); an average of 7, about 0.2 mm in width and an average of 18 cm in length (shortest at terminus), 138B in color, glabrous surface, pedicel; an average of 5 mm in length and 0.2 mm in width, very fine and wiry, 138B in color, glabrous surface.

Reproductive organs:

*Androecium*.—Anthers; 3, an average of 2 mm in length and 0.75 mm in width, 172A in color, basifixed on very fine, translucent filament, pollen; moderate in quantity and 162C in color.

*Gynoecium*.—Pistil; 1, 2 plumose stigmas on short, fine styles adnate to ovary, stigma N79B to N79C in color, an average of 1.5 mm in length and 0.25 mm in width, ovary; 1-locular, superior, an average of 2.5 mm in length and 1 mm in with, 149D in color.

It is claimed:

1. A new and distinct cultivar of *Panicum* plant named 'Noneulby' as herein illustrated and described.

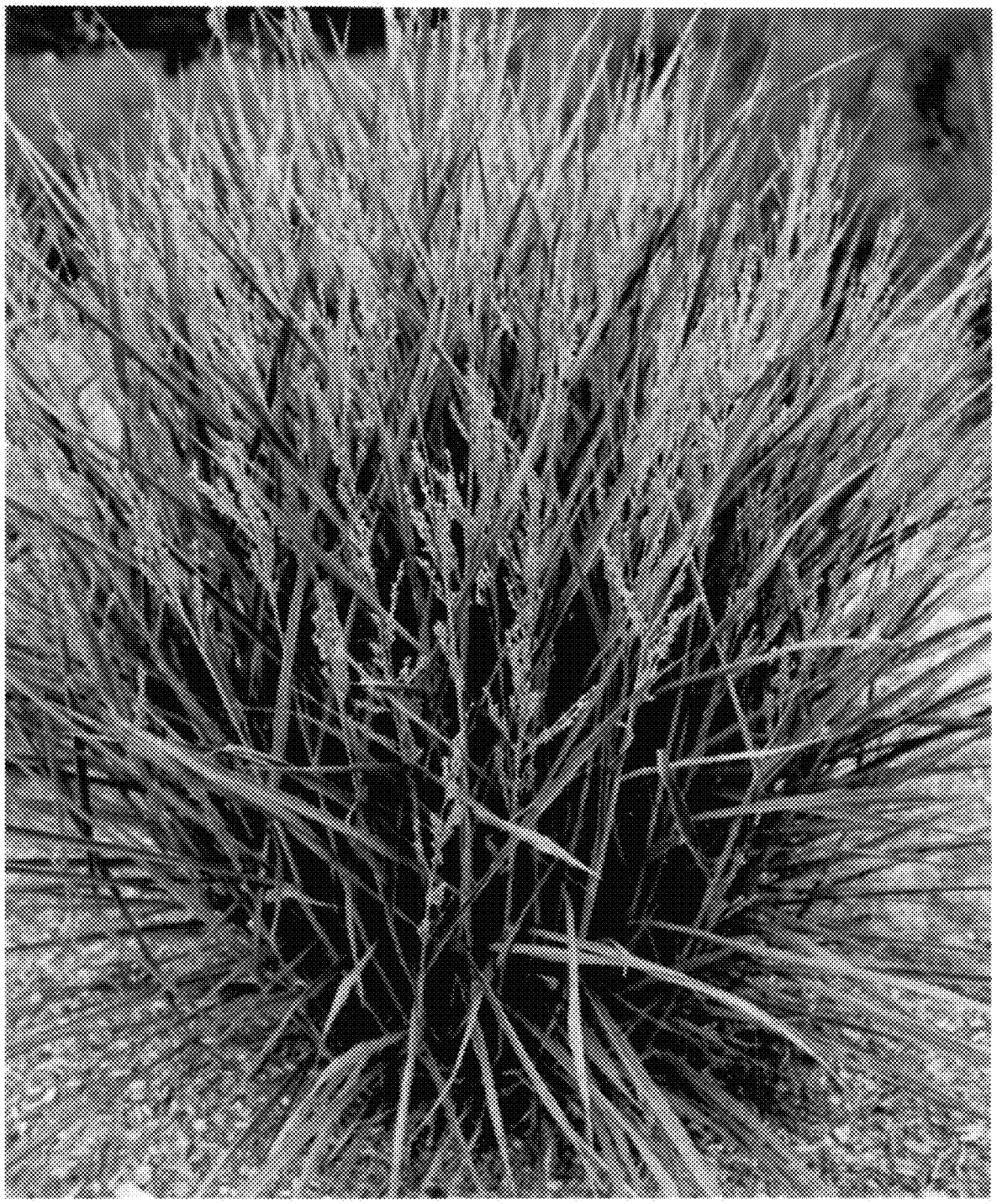

* * * * *